(12) United States Patent
Kanemitsu

(10) Patent No.: US 7,177,393 B2
(45) Date of Patent: Feb. 13, 2007

(54) X-RAY IMAGING APPARATUS

(75) Inventor: Shingo Kanemitsu, Tochigi-ken (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 0 days.

(21) Appl. No.: 11/177,404

(22) Filed: Jul. 11, 2005

(65) Prior Publication Data
US 2006/0018431 A1    Jan. 26, 2006

(30) Foreign Application Priority Data
Jul. 21, 2004    (JP)    ............... 2004-213275

(51) Int. Cl.
H05G 1/56    (2006.01)
A61B 6/04    (2006.01)

(52) U.S. Cl. ............... 378/117; 378/114; 378/209; 5/601

(58) Field of Classification Search ............... 378/20, 378/68, 114–117, 195, 196, 177, 208–9; 5/601
See application file for complete search history.

(56) References Cited

U.S. PATENT DOCUMENTS 4,775,993 A * 10/1988 Kaul et al. ............... 378/117
5,400,382 A * 3/1995 Welt et al. ............... 378/69
5,615,430 A * 4/1997 Nambu et al. ............... 5/600
6,409,381 B1 * 6/2002 Siebenhaar et al. ......... 378/197
6,486,573 B2 * 11/2002 Yagi et al. ............... 307/328
2001/0040939 A1 * 11/2001 Kobayashi ............... 378/177
2002/0172326 A1 * 11/2002 Yamayoshi ............... 378/97
2003/0021386 A1 * 1/2003 Tanaka ............... 378/198

* cited by examiner

Primary Examiner—Edward J. Glick
Assistant Examiner—Anastasia S. Midkiff
(74) Attorney, Agent, or Firm—Oblon, Spivak, McClelland, Maier & Neustadt, P.C.

(57) ABSTRACT

An X-ray imaging apparatus includes a body unit including a bed unit where an object is put, an X-ray irradiation unit configured to irradiate an X-ray to the object and an X-ray detector configured to detect the X-ray passing through the object, an input unit configured to input control information to control at least part of operation of the body unit, a selection unit configured to select ON or OFF of a lock mode and a controller configured to determine at least part of the control information is locked when the lock mode is ON and the at least part of the control information is released when the lock mode is OFF.

17 Claims, 5 Drawing Sheets

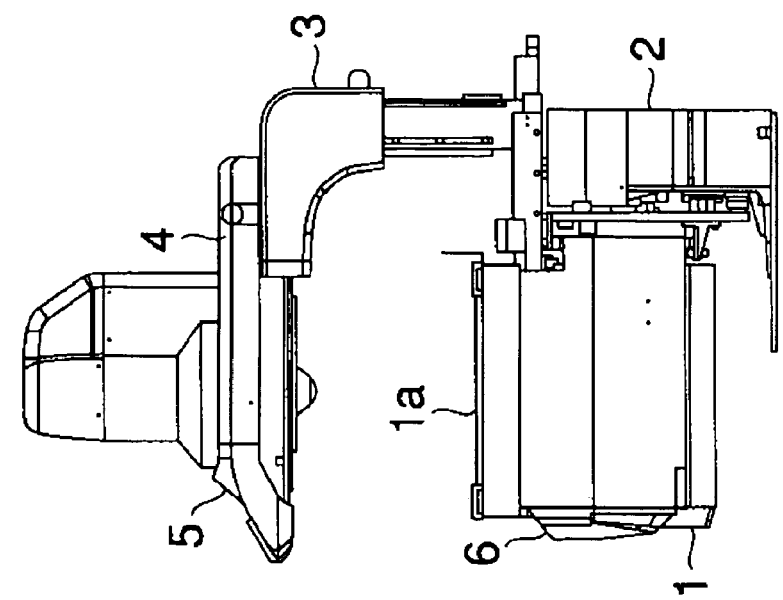
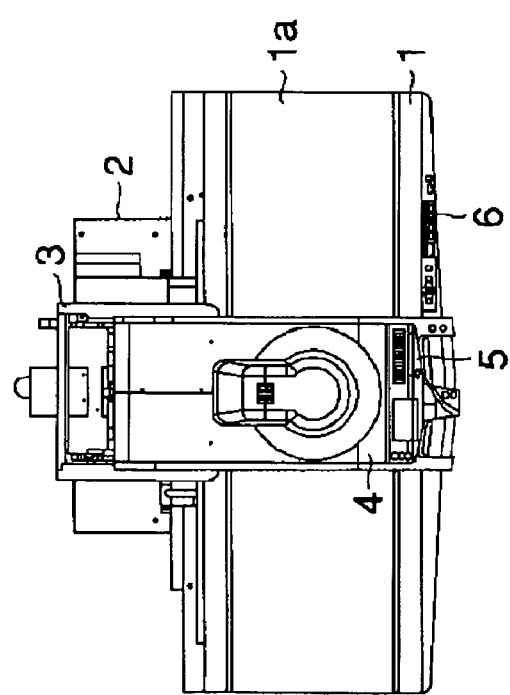
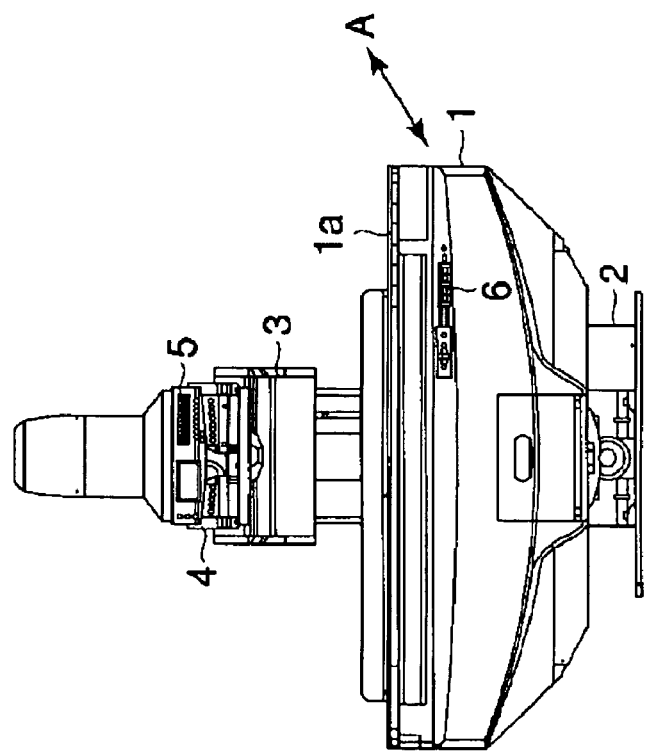
FIG. 1C
FIG. 1B
FIG. 1A

X-RAY IMAGING APPARATUS

CROSS-REFERENCE TO RELATED APPLICATIONS

This application is based upon and claims the benefit of priority from prior Japanese Patent Application No. P2004-213275 filed on Jul. 21, 2004, the entire contents of which are incorporated herein by reference.

FIELD OF THE INVENTION

The present invention relates to an X-ray imaging apparatus.

BACKGROUND

In a tableside controlled X-ray imaging apparatus, an operation panel that is operated by a doctor or a radiological technologist is located near a bed part, for example. Although the operation panel is located at a position so as to be easily operated, such a location is a position where a patient can also touch easily. A tableside controlled X-ray imaging apparatus is disclosed in Japanese Patent Publication (Kokai) No. 7-327984.

Switches to instruct execution of fluoroscopy or radiography, for example, are arranged on the operation panel. When the patient who is laid on a table top touches the switches, X-ray irradiation may be performed.

For this reason, using a conventional X-ray imaging apparatus, while the patient is laid on the table top, the doctor or the radiological technologist is not allowed to leave the X-ray imaging apparatus. However, it is a personal agreement and may not be perfectly protected.

As described above, it is difficult to prevent the patient from touching the operation panel with the conventional tableside controlled X-ray imaging apparatus, and unnecessary X-ray irradiation may be performed, for example.

In addition, if the operation panel is located at a position where the patient cannot touch the panel easily, it is difficult also for the doctor or the radiological technologist to operate.

SUMMARY OF THE INVENTION

One object of the present invention is to ameliorate at least one of the above-mentioned problems, and there is provided an X-ray imaging apparatus which can reduce operation mistakes without deterioration in performance. According to one aspect of the present invention, there is provided an X-ray imaging apparatus including a body unit including a bed unit where an object is put, an X-ray irradiation unit configured to irradiate an X-ray to the object and an X-ray detector configured to detect the X-ray passing through the object, an input unit configured to receive input control information to control at least part of operation of the body unit, a selection unit configured to select ON or OFF of a lock mode, and a controller configured to determine the at least part of the control information which is locked when the lock mode is ON and the at least part of the control information which is not locked when the lock mode is OFF.

BRIEF DESCRIPTION OF THE DRAWINGS

In the drawings:

FIG. 1A is a front view of an X-ray imaging apparatus in a first embodiment;

FIG. 1B is a top view of the X-ray imaging apparatus in the first embodiment;

FIG. 1C is a side view of the X-ray imaging apparatus in the first embodiment;

DETAILED DESCRIPTION OF EXEMPLARY EMBODIMENTS

Figure 2:
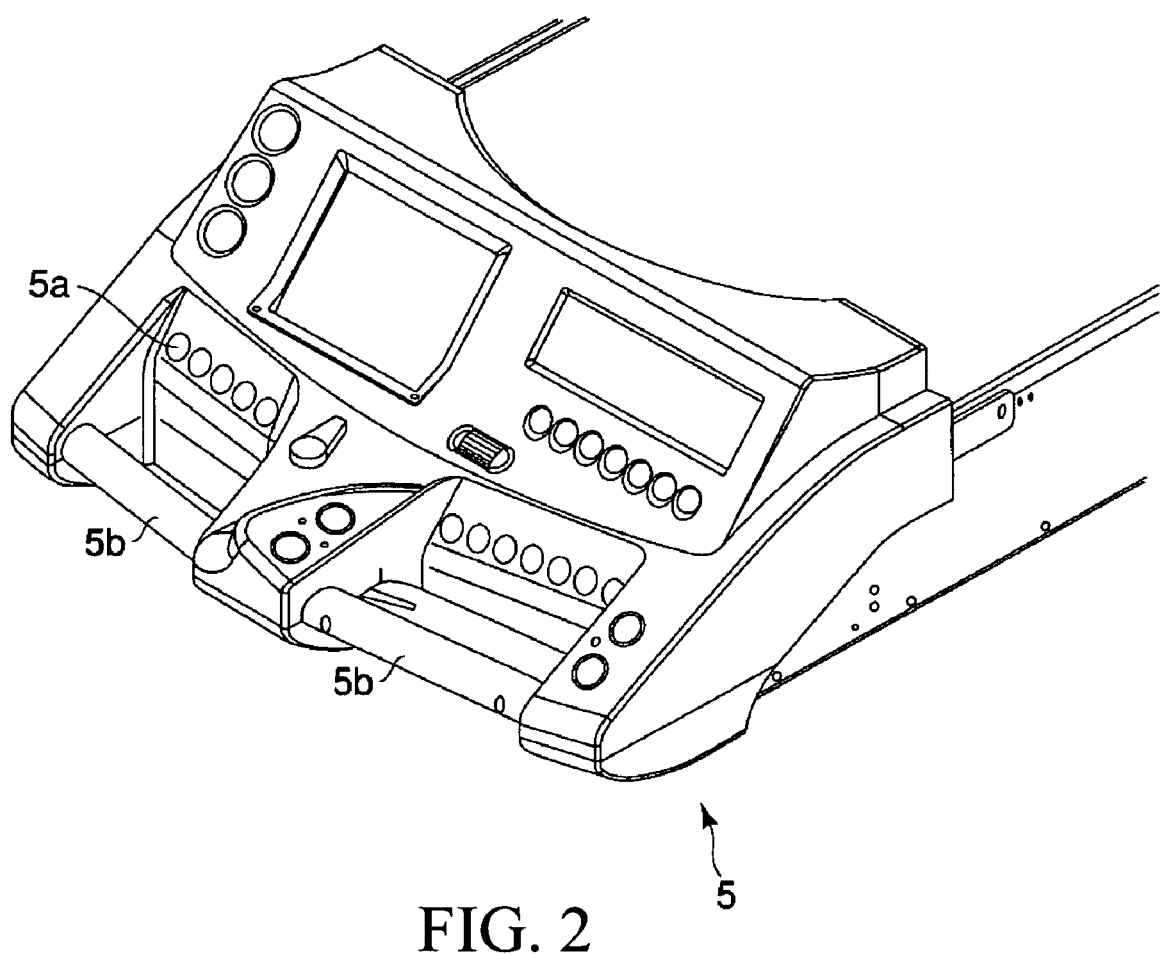
FIG. 2 is a perspective view of a spot side operation part of the X-ray imaging apparatus shown in FIGS. 1A through 1C.

Hereafter, a first embodiment is explained with reference to the figures. FIGS. 1A through 1C are overviews of an X-ray imaging apparatus in the first embodiment. FIG. 1A is a front view, FIG. 1B is a top view and FIG. 1C is a side view of the X-ray imaging apparatus.

As shown in FIGS. 1A through 1C, the X-ray imaging apparatus in the first embodiment includes a bed part 1, a base part 2, a gantry 3, an X-ray detector 4, a detector control panel 5, and a bedside (tableside) control panel 6.

The bed part 1 includes a table top 1a on an upper part. A patient is laid on the table top 1a. In the bed part 1, a table top moving mechanism part 11 shown in FIG. 3 to move the table top 1a is located. Moreover, in the bed part 1, an X-ray tube 7 which irradiates an X-ray to the patient on the table top 1a and a beam limiting device 8 which adjusts an X-ray irradiation range are located.

The base part 2 that is fixed to a floor in an operating room where the X-ray imaging apparatus is located supports the bed part 1. The base part 2 includes a tilting mechanism part 10 which tilts the table top 1a in a direction as indicated by arrow A.

The gantry 3 is attached to the bed part 1. The gantry 3 supports X-ray detector 4 to be moved in a horizontal direction and a perpendicular direction to the bed part 1. The gantry 3 includes a power assistant mechanism part which performs power assistance of movement of the X-ray detector 4.

The X-ray detector 4 changes an X-ray irradiated through the patient into an electric signal to make an X-ray image.

The detector control panel 5 and the bedside control panel 6 receive instruction from the doctor or the radiological technologist. The detector control panel 5 is located at the end of the X-ray detector 4, and is mainly used by the doctor, for example. The bedside control panel 6 is located at the side of the bed part 1, and is mainly used by the radiological technologist, for example.

Figure 3:
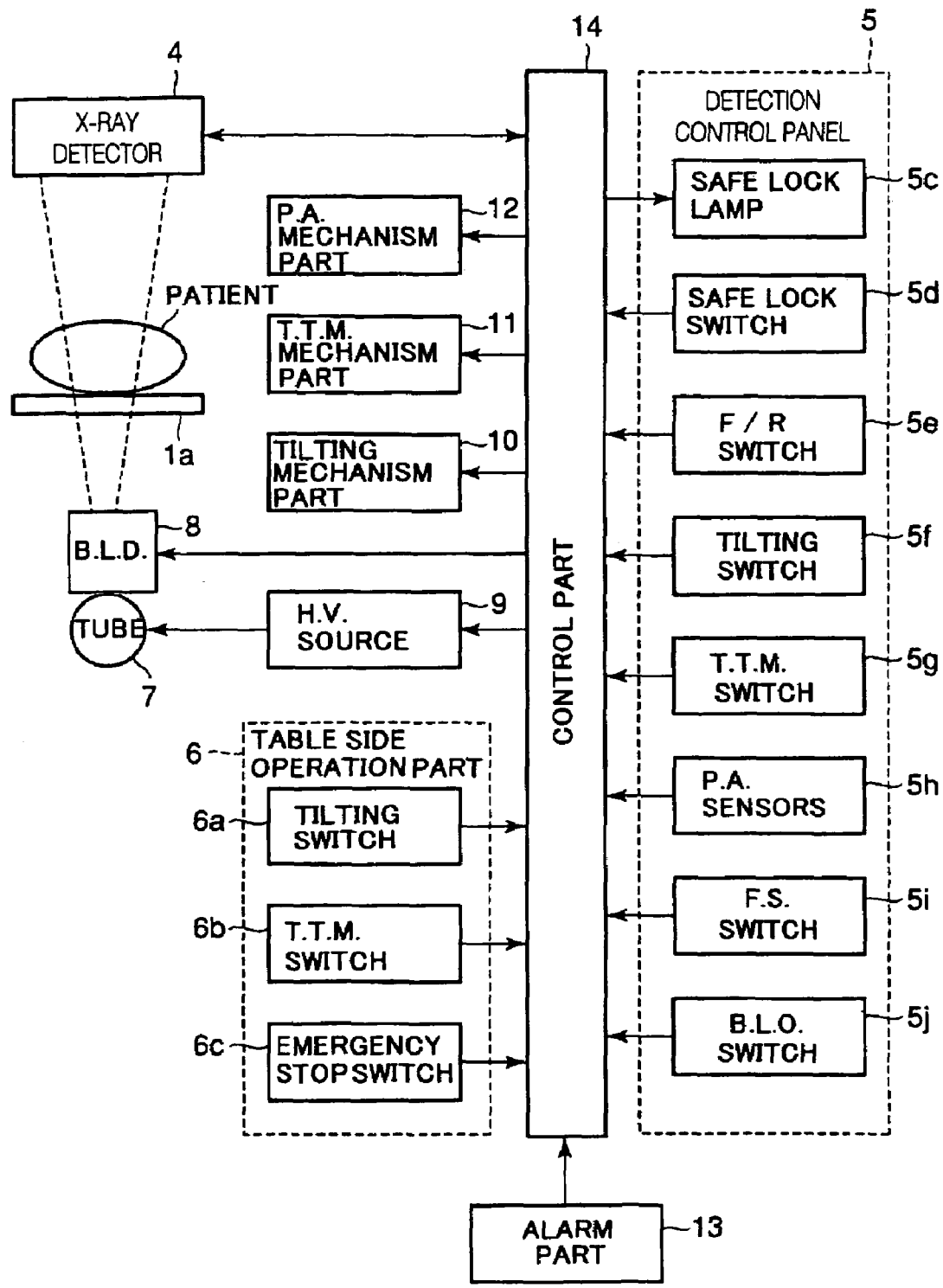
FIG. 3 is a block diagram of the X-ray imaging apparatus shown in FIGS. 1A through 1C.

FIG. 2 is a expanded perspective view of the detector control panel 5 shown in FIGS. 1A through 1C. As shown in FIG. 2, the detector control panel 5 includes an operation button, a control lever and a display part. One of the operation buttons is a safe lock button 5a. Under the safe lock button 5a, a safe lock switch 5d and a safe lock lamp 5c shown in FIG. 3 are located. The safe lock button 5a is pushed to turn on/off the safe lock switch 5d and a light of the safe lock lamp 5c.

Moreover, the detector control panel 5 includes a handle 5b. Inside the handle 5b, power assistant sensors 5h shown in FIG. 3 are arranged. The power assistant sensors 5h include a plurality of sensors that detect a direction and strength of forces resulting from inputs at the handle 5b.

FIG. 3 is a block diagram of the X-ray imaging apparatus in the first embodiment. To simplify an explanation, further explanations are omitted by attaching the same reference numbers in FIG. 3 as illustrated in FIGS. 1A through 1C. As shown in FIG. 3, the X-ray detector 4, the detector control panel 5, the bedside control panel 6, the beam limiting device 8, a high voltage generator 9, the tilting mechanism part 10, the table top moving mechanism part 11, the power assistant mechanism part 12, and an alarm part 13 are electrically connected to a control part 14 directly or indirectly, respectively.

The detector control panel 5 includes the safe lock lamp 5c, the safe lock switch 5d, a fluoroscopy/radiography switch 5e and tilting switch 5f, a table top move switch 5g, the power assistant sensors 5h, a format selection switch 5i and a beam limiting operation switch 5j, for example. The fluoroscopy/radiography switch 5e and the tilting switch 5f, the table top move switch 5g, the format selection switch 5i and the beam limiting operation switch 5j are turned on by pushing corresponding buttons located on the detector control panel 5.

The bedside control panel 6 includes a tilting switch 6a, a table top move switch 6b and an emergency stop switch 6c, and the switches are turned on by pushing corresponding buttons located on the bedside control panel 6.

The high voltage generator 9 generates high voltage so that the X-ray tube 7 irradiates the X-ray.

The alarm part 13 outputs alarm sound.

The control part 14 includes a computer and peripheral devices, such as a memory. The control part 14 controls the X-ray detector 4, the beam limiting device 8, the high voltage generator 9, the tilting mechanism part 10, the table top move mechanism part 11, the power assistant mechanism part 12 and the alarm part 13 according to the instruction inputted by the user operating the detector control panel 5 and/or the bedside control panel 6.

Next, operation of the X-ray imaging apparatus is explained. After the X-ray imaging apparatus starts, the control part 14 performs processing as shown in FIG. 4, in order to receive the instruction by the user.

Figure 4:
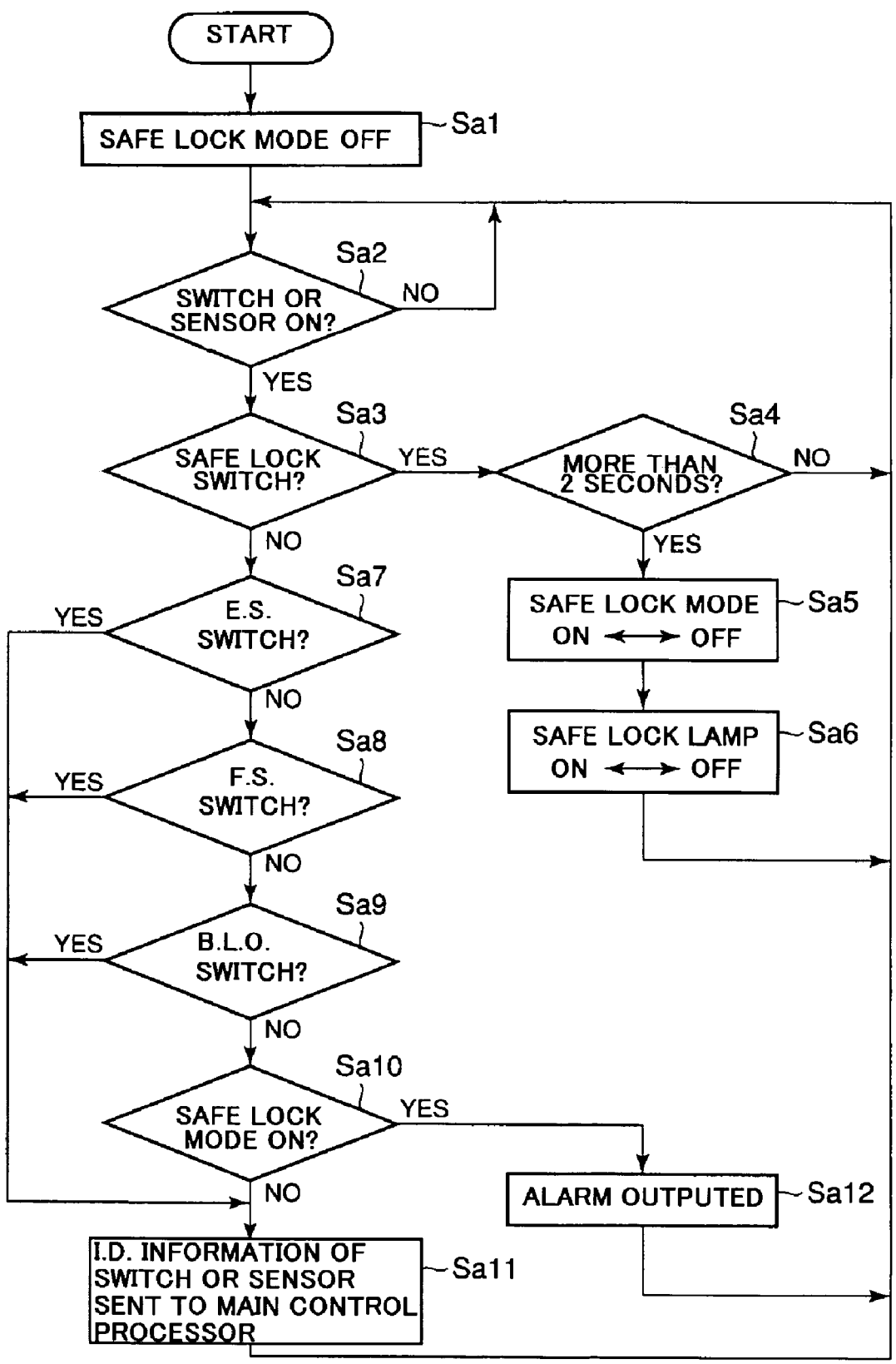
FIG. 4 is a flow chart to receive an operation instruction from an user.

In Step Sa1 in FIG. 4, the control part 14 initially sets a safe lock mode as OFF state. The safe lock mode is a mode which determines a lock state of the detector control panel 5, and when the safe lock mode is ON, at least one operation of the detector control panel 5 is locked, and when the safe lock mode is OFF, the lock of the operation is released.

In Step Sa2, the control part 14 holds to receive ON signal from the switches or the sensors of the detector control panel 5 and the bedside control panel 6. When one of the switches or the sensors turn on, the control part 14 goes forward to Step Sa3 from Step Sa2.

In Step Sa3, the control part 14 checks whether the switch turned on is the safe lock switch 5d. When the turned on switch is the safe lock switch 5d, the control part 14 goes forward to Step Sa4 from Step Sa3. In Step Sa4, the control part 14 further checks whether a period while the safe lock button 5a corresponding to the safe lock switch 5d is pushed is more than 2 seconds.

When the button of the safe lock switch 5d is pushed for a period not more than 2 seconds, the control part 14 returns from Step Sa4 to Sep Sa2 to hold. That is, at this time, the control part 14 ignores the operation of the safe lock button 5a. On the other hand, when the safe lock button 5a is pushed for a period more than 2 seconds, namely when the safe lock button is pushed for a long time, the control part 14 goes forward to Step Sa5 from Step Sa4. In Step Sa5, the control part 14 changes ON/OFF of the safe lock mode. In Step Sa6, the control part 14 changes lighting of the safe lock lamp 5c. That is, when the safe lock mode is OFF and the safe lock button 5a is pushed for a long time, the control part 14 changes the safe lock mode to ON and the turned off safe lock lamp 5c to turn on. On the contrary, when the safe lock mode is OFF and the safe lock button 5a is pushed for a long time, the control part 14 changes the safe lock mode to OFF and the turned on safe lock lamp 5c to turn off. After this, the control part 14 goes back to Step Sa2 to hold.

In Step Sa3, when the switch switched on is not the safe lock switch, the control part 14 goes forward to Step Sa7. In Step Sa7, Step Sa8 and Step Sa9, the control part 14 checks whether the switch switched on is one of the emergency stop switch 6c, the format selection switch 5i and the beam limiting operation switch 5j. When the switch switched on is not any of these switches, and in other words, when the switched switch is one of the fluoroscopy/radiography switch 5e, the tilting switch 5f, the table top move switch 5g, the power assistant sensors 5h, the tilting switch 6a and the table top move switch 6b, for example, the control part 14 goes forward to Step Sa10 from Step Sa9. In Step Sa10, the control part 14 checks whether the safe lock mode is ON. When the safe lock mode is OFF, the control part 14 goes forward to Step Sa11 from Step Sa10. When the switch switched on is one of the emergency stop switch 6c, the format selection switch 5i and the beam limiting operation switch 5j, the control part 14 goes forward to Step Sa11 from either Step Sa7, Step Sa8 and Step Sa9. That is, when any one of the emergency stop switch 6c, the format selection switch 5i and the beam limiting operation switch 5j turns on, the control part 14 goes forward to Step Sa11 regardless of the state of the safe lock mode. Since the emergency stop switch 6c is a switch which is used in an imperative situation, it is desired that the emergency stop switch 6c can be used any time. The format selection switch 5i is used for selecting a format among a plurality of formats, each of which corresponds to an X-ray irradiation range, such as a whole range or half range of X-ray detector. The format selection switch 5i and the beam limiting operation switch 5j are switches that are related to X-ray limiting. Since the operator operates the X-ray limiting frequently, the operation can be performed regardless of the safe lock mode. However, the format selection switch 5i and the beam limiting operation switch 5j may be locked when the safe lock mode is ON. When one of the fluoroscopy/radiography switch 5e and the tilting switch 5f, the table top move switch 5g, the power assistant sensors 5h, the tilting switch 6a and the table top move switch 6b turn on, the control part 14 goes forward to Step Sa11 only when the safe lock mode is OFF.

In Step Sa11, the control part 14 sends identification information of the switch switched on or the sensors to a main control processor. After that, the control part 14 goes back to Step Sa2.

The control part 14 performs the above-mentioned processing shown in FIG. 4 and further performs a main control processing as another task. In the main control processing, the control part 14 performs the following controls, respectively, according to the switch switched on. The control part 14 makes the X-ray detector 4 active and starts to supply the high voltage to the X-ray tube 7 from the high voltage generator 9, when the fluoroscopy/radiography switch 5e turns on. When the tilting switches 5f and 6a turn on, the control part 14 controls the tilting mechanism part 10 to raise the bed part 1. The gantry 3 and the X-ray detector 4 are also raised according to the bed part 1 being raised. When the table top move switches 5g and 6b turn on, the control part 14 controls the table top move mechanism part 11 to move the table top 1a. When one of power assistant sensors 5h turns on, the control part 14 controls the power assistant mechanism part 12 to assist the movement of the X-ray detector 4 in a direction determined by the sensors. The direction is a far or near direction to the patient and/or a longitudinal direction of the table top, etc. When the format selection switch 5i turns on, the control part 14 chooses a format.

When the beam limiting operation switch 5j turns on, the control part 14 controls the beam limiting device 8 to adjust the X-ray irradiation range. When the emergency stop switch 6c turns on, the control part 14 performs emergency stop of operation of each part, such as the high voltage generator 9, the tilting mechanism part 10, the table top move mechanism part 11 and the power assistant mechanism part 12.

Figure 5:
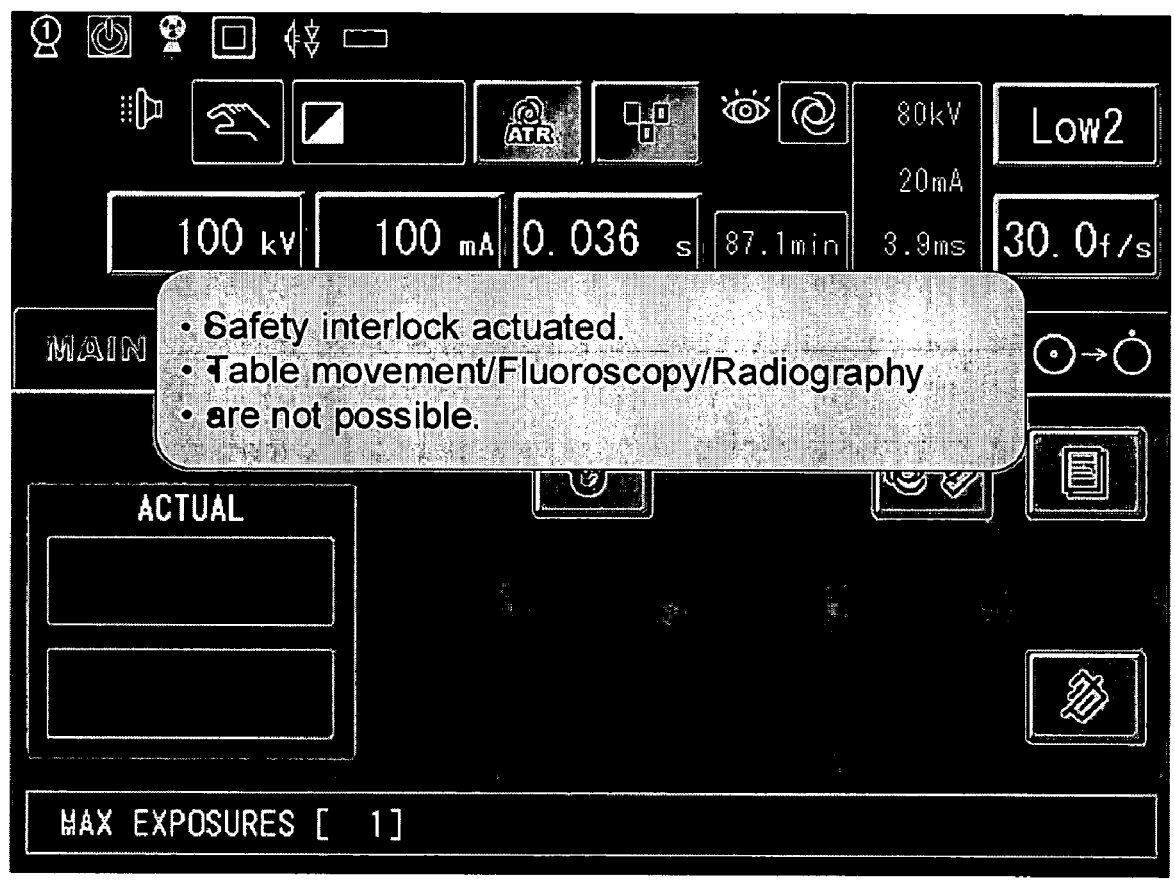
FIG. 5 is an illustration displayed during a safe lock mode.

When one of the fluoroscopy/radiography switch 5e, the tilting switch 5f, the table top move switch 5g, the power assistant sensors 5h, the tilting switch 6a and the table top move switch 6b turn on, while the safe lock mode is OFF, the above-mentioned operation is performed. However, when the safe lock mode is ON, the control part 14 goes forward to Step Sa12 from Step Sa10. The control part 14 controls the alarm part 13 to output the alarm sound in Step Sa12. In addition, without Step Sa11, the control part 14 goes back to Step Sa2. That is, while the safe lock mode is ON, when one of the fluoroscopy/radiography switch 5e, the tilting switch 5f, the table top move switch 5g, the power assistant sensors 5h, the tilting switch 6a and the table top move switch 6b turn on, the alarm sound outputs without performing each corresponding operation. Moreover, in addition to or instead of the alarm sound, the alarm part 13 may display a warning message shown in FIG. 5 on a display, for example.

Thus, according to the X-ray imaging apparatus in the first embodiment, when the user pushes the safe lock button 5a for more than 2 seconds, the safe lock mode can be turned on and off. In addition, since the safe lock lamp 5c turns on and off according to operation ON/OFF of the safe lock mode, the user can easily recognize the state of the safe lock mode.

And when the safe lock mode is ON, even if the fluoroscopy/radiography switch 5e turns on, the X-ray irradiation from X-ray tube 7 is not performed. Therefore, when the safe lock mode is set to ON while the doctor or the radiological technologist leaves the X-ray imaging apparatus, even if the patient touches the detector control panel 5 or the bedside control panel 6, such as the fluoroscopy/radiography switch 5e, unnecessary X-ray irradiation is not performed.

Moreover, in the first embodiment, when the safe lock mode is ON, even if the tilting switches 5f and 6a or the table top move switches 5g and 6b turn on, the tilting mechanism part 10 or the table top move mechanism part 11 does not operate. Therefore, when the safe lock mode is set to ON when the doctor or the radiological technologist leaves the X-ray imaging apparatus, even if the patient touches the detector control panel 5 and the bedside control panel 6, such as the tilting switches 5f and 6a or the table top move switches 5g and 6b, tilting of the bed part 1 or movement of table top 1a is not performed.

Moreover, in the first embodiment, when the safe lock mode is ON, even if either of the power assistant sensors 5h turns on, the power assistant mechanism part 12 does not operate. Therefore, when the safe lock mode is set to ON when the doctor or the radiological technologist leaves the X-ray imaging apparatus, even if the patient grasped the handle 5b and the power assistant sensors 5h turn on, power assistance of movement of the X-ray detector 4 is not performed, and the X-ray detector 4 does not move easily. As shown in FIG. 1, since the detector control panel 5 is located on an upper side of the patient laid on the table top 1a, when the patient grasps handle 5b by accident, the patient pulls the handle 5b to the patient's side in many cases. In such a case, the power assistance works in such a direction that the X-ray detector 4 comes to the patient. For this reason, when the patient pulls the handle 5b even a little, the X-ray detector 4 may approach the patient rapidly, which may make the patient surprised, however such a situation can be reduced by the first embodiment. Especially, in a case when movement of the X-ray detector 4 in the far and near direction can be locked, the above-mentioned situation can be reduced and it is very useful.

Moreover, in the first embodiment, since the alarm sound is outputted when the safe lock mode is ON and one of the fluoroscopy/radiography switch 5e, the tilting switch 5f, the table top move switch 5g, the power assistant sensors 5h, the tilting switch 6a and the table top move switch 6b turn on as mentioned above, the doctor and the radiological technologist can notice a situation where the patient touches the detector control panel 5 or the bedside control panel 6. Thereby, the doctor and the radiological technologist can be reminded to observe the patient's action carefully.

The following various modifications may be possible according to the first embodiment. For example, the operation for turning off the safe lock mode may not be limited to the long press of a button, but may be just to push a button again, or may be to push several buttons simultaneously, etc. The X-ray imaging apparatus shown in FIGS. 1A through 1C may include a structure which can attach an X-ray tube on X-ray detector 4 side and position a film under the table top 1a to obtain an X-ray image on the film. In this situation, it is possible to control X-ray irradiation from the X-ray attached on X-ray detector 4 side as well as the X-ray tube 7.

The present invention may be not limited to the above embodiments, and various modifications may be made without departing from the spirit or scope of the general inventive concept. Although the above embodiment and modification may include various steps or various elements, one or more steps or elements may be arbitrarily selected. For instance, one or more steps or elements described as the embodiment or modification may be omitted. In addition, some elements in different embodiments may be combined. According to the above embodiment, even if a first switch is touched by the patient, it can prevent irradiating the X-ray certainly. Since the first switch is arranged in such a position that the patient can touch, the operationality is not deteriorated. Moreover, in the first embodiment, although the X-ray detector is shown as a detector which detects the X-ray passing through the patient and changes the X-ray into an the electric signal, instead of the X-ray detector, an indirect change type flat panel detector which changes the X-ray into an optical signal once to change the optical signal to an electric signal or a direct type flat panel detector which changes X-rays into a electric signal directly may be used. As another modification, the following feature may be applied. When the safe lock mode is ON, an operation of the detector control panel 5 is locked, however an operation of the bedside control panel 6 may not be locked.

What is claimed is:
1. An X-ray imaging apparatus, comprising:
   a body unit including a bed unit where an object is put, an X-ray irradiation unit configured to irradiate an X-ray to the object, and an X-ray detector configured to detect the X-ray passing through the object;

an input unit configured to input control information related to control at least part of operation of the body unit;

a selection unit configured to select ON or OFF of a lock mode;

a controller configured to determine at least part of the control information is locked when the lock mode is ON and the at least part of the control information is released when the lock mode is OFF;

wherein the X-ray irradiation unit is located under the bed unit and the X-ray detector is located opposite to the X-ray irradiation unit such that the object is located between the X-ray irradiation unit and the X-ray detector, wherein the input unit is attached to the X-ray detector; and further comprising:

a bedside control panel, attached to the bed unit, configured to input control information, and wherein the at least part of the control information inputted from the input unit attached to the X-ray detector is locked when the lock mode is ON and the control information inputted from the bedside control panel attached to bed unit is not locked even when the lock mode is ON.

2. An X-ray imaging apparatus, comprising:

a body unit including a bed unit where an object is put, an X-ray irradiation unit configured to irradiate an X-ray to the object, and an X-ray detector configured to detect the X-ray passing through the object;

an input unit configured to input control information related to control at least part of operation of the body unit;

a selection unit configured to select ON or OFF of a lock mode;

a controller configured to determine at least part of the control information is locked when the lock mode is ON and the at least part of the control information is released when the lock mode is OFF; and an emergency stop unit configured to stop at least part of operation of the body unit, and wherein the controller does not lock the control information related to control of the emergency stop unit even when the lock mode is ON.

3. An X-ray imaging apparatus, comprising:

a body unit including a bed unit where an object is put, an X-ray irradiation unit configured to irradiate an X-ray to the object, and an X-ray detector configured to detect the X-ray passing through the object;

an input unit configured to input control information related to control at least part of operation of the body unit;

a selection unit configured to select ON or OFF of a lock mode;

a controller configured to determine at least part of the control information is locked when the lock mode is ON and the at least part of the control information is released when the lock mode is OFF; and a beam limiting unit configured to adjust an X-ray irradiation range irradiated from the X-ray irradiation unit, and wherein the controller does not lock the control information related to control of the beam limiting unit even when the lock mode is ON.

4. An X-ray imaging apparatus, comprising:

a body unit including a bed unit where an object is put, an X-ray irradiation unit configured to irradiate an X-ray to the object, and an X-ray detector configured to detect the X-ray passing through the object;

an input unit configured to input control information related to control at least part of operation of the body unit;

a selection unit configured to select ON or OFF of a lock mode;

a controller configured to determine at least part of the control information is locked when the lock mode is ON and the at least part of the control information is released when the lock mode is OFF; and a format selection unit configured to select a format, and wherein the controller does not lock the control information related to control of the format selection unit even when the lock mode is ON.

5. The X-ray imaging apparatus according to claim 2, wherein the X-ray irradiation unit is located under the bed unit and the X-ray detector is located opposite to the X-ray irradiation unit such that the object is located between the X-ray irradiation unit and the X-ray detector.

6. The X-ray imaging apparatus according to claim 5, wherein the input unit is attached to the X-ray detector.

7. The X-ray imaging apparatus according to claim 2, wherein the controller locks the input control information related to control of an X-ray irradiation when the lock mode is ON.

8. The X-ray imaging apparatus according to claim 2, further comprising a tilting mechanism configured to tilt the bed unit, and wherein the controller locks the control information related to control of tilting of the bed unit when the lock mode is ON.

9. The X-ray imaging apparatus according to claim 2, further comprising a table top move mechanism configured to move a table top of the bed unit, and wherein the controller locks the control information related to control of movement of the table top when the lock mode is ON.

10. The X-ray imaging apparatus according to claim 2, further comprising a beam limiting unit configured to adjust an X-ray irradiation range irradiated from the X-ray irradiation unit, and wherein the controller locks the control information related to control of the beam limiting unit when the lock mode is ON.

11. The X-ray imaging apparatus according to claim 2, further comprising a power assistant mechanism configured to assist movement of the input unit in a direction of a force input at a handle of the input unit, and wherein the controller locks the control information related to control of the power assistant mechanism when the lock mode is ON.

12. The X-ray imaging apparatus according to claim 11, wherein the power assistant mechanism assists movement in a far or near direction to the object, and the controller locks the control information related to movement of the input unit in the far or near direction when the lock mode is ON.

13. The X-ray imaging apparatus according to claim 2, further comprising an alarm unit configured to give an alarm when the input unit is operated when the lock mode is ON.

14. The X-ray imaging apparatus according to claim 13, wherein the alarm unit outputs alarm sound.

15. The X-ray imaging apparatus according to claim 13, wherein the alarm unit displays a warning on a display unit.

16. The X-ray imaging apparatus according to claim 2, wherein the selection unit is a selection button that is a part of the input unit.

17. The X-ray imaging apparatus according to claim 16, wherein the selection button includes:

a selection switch configured to change ON or OFF of the lock mode; and a selection lamp indicating which ON or OFF of the lock mode is selected.

* * * * *